United States Patent [19]

Corley

[11] Patent Number: 5,233,002

[45] Date of Patent: Aug. 3, 1993

[54] DIALKYLIDENECYCLOBUTANE/-BISIMIDE/TRIENE COMPOSITION

[75] Inventor: Larry S. Corley, Houston, Tex.

[73] Assignee: Shell Oil Company, Houston, Tex.

[21] Appl. No.: 890,061

[22] Filed: May 28, 1992

Related U.S. Application Data

[63] Continuation-in-part of Ser. No. 733,947, Jul. 22, 1991, Pat. No. 5,147,953.

[51] Int. Cl.$^5$ .............................................. C08F 12/32
[52] U.S. Cl. ...................................... 526/262; 524/548; 526/308; 526/335; 526/336; 528/322
[58] Field of Search ............... 526/262, 335, 336, 308; 528/322; 524/548

[56] References Cited

U.S. PATENT DOCUMENTS

| | | | |
|---|---|---|---|
| 4,645,814 | 2/1987 | Grubbs | 526/252 |
| 4,730,030 | 3/1988 | Hahn et al. | 526/262 |
| 4,973,636 | 11/1990 | Corley | 526/262 |
| 5,086,139 | 2/1992 | Corley | 526/262 |

OTHER PUBLICATIONS

Godt et al., "Double-Stranded Molecules," *Angew. Chem.* 28, 1680–1682 (1989).

*Primary Examiner*—Harold D. Anderson

[57] ABSTRACT

A composition comprising a 1,2-dialkylidenecyclobutane such as 1,2-dimethylenecyclobutane, a triene such as myrcene and a polyimide such as a bismaleimide can be thermally cured to a tough copolymer having a high glass transition temperature.

19 Claims, No Drawings

DIALKYLIDENECYCLOBUTANE/BISIMIDE/TRIENE COMPOSITION

CROSS-REFERENCE TO RELATED APPLICATION

This is a continuation-in-part of Ser. No. 733,947, filed Jul. 22, 1991, now U.S. Pat. No. 5,147,953.

BACKGROUND OF THE INVENTION

This invention relates to thermosettable resin compositions. In one embodiment, the invention relates to enhancement of the properties of bisimide/triene compositions.

Advanced composites are high-performance materials made up of a fiber-reinforced thermoplastic or thermosettable material. Thermosettable materials useful in advanced composites applications must meet a set of demanding property requirements. For example, such materials optimally have good high-temperature properties such as high (above 200° C.) cured glass transition temperature and good mechanical strength. For ease of processing prepregs for composite parts, the uncured material will ideally have a low (below 120° C.) melting temperature and a wide temperature range of processable viscosity (a wide "processing window").

Bismaleimide resins have superior high-temperature properties but are very brittle and further tend, because of their high softening points, to require solvents in order to be readily processable. In addition, standard cured bismaleimide resins tend to have high (in the 5-7% range) 93° C. water absorption. Addition of thermoplastic or cyanate-terminated oligomers to bismaleimides increases the toughness but produces uncured mixtures so high in viscosity that fiber impregnation and processing by standard thermoset techniques are difficult.

It is thus an object of the invention to provide new thermoset resin materials. In one aspect, it is an object of the invention to provide comomomers which provide low-melting bismaleimides which cure to high-Tg, tough resins.

SUMMARY OF THE INVENTION

According to the invention, a composition is provided comprising a 1,2-dialkylidenecyclobutane, a bisimide and a reactive triene which is characterized by a conjugated diene moiety capable of Diels-Alder reaction with the bisimide and an isolated double bond. The invention copolymers have superior toughness and can be melt-processed for composites applications.

DETAILED DESCRIPTION OF THE INVENTION

The invention composition includes a bisimide of an unsaturated dicarboxylic acid. The preferred bisimides are N,N'-bisimides of unsaturated dicarboxylic acids which can be represented by the formula

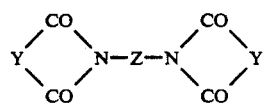

in which Y is a substituted or unsubstituted divalent group containing at least 2 carbon atoms, preferably 2 to 6 carbon atoms, and a carbon-carbon double bond, and Z is a divalent group containing at least 1 and generally about 1 to 40 carbon atoms. Z can be aliphatic, cycloaliphatic, aromatic or heterocyclic. A preferred class of bisimides comprises bismaleimides derived from aromatic amines and can be represented by the formula

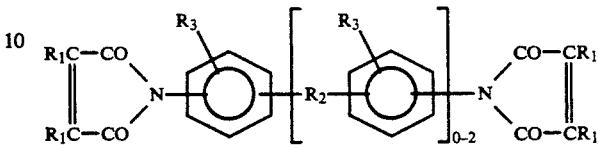

in which each $R_1$ is selected independently from H, $C_{1-2}$ alkyl or halide; $R_2$ is selected from divalent hydrocarbon radicals containing from about 1 to about 10 carbon atoms, —O—, —$SO_2$—, —COO—, —CONH—, —CO— and —S—; and each $R_3$ is selected independently from H, $C_{1-3}$alkyl and halide. The aromatic rings may alternatively be heterocyclic.

Examples of such bisimides include
1,2-bismaleimidoethane
1,6-bismaleimidohexane
1,3-bismaleimidobenzene
1,4-bismaleimidobenzene
2,4-bismaleimidotoluene
4,4'-bismaleimidodiphenylmethane
4,4'-bismaleimidodiphenylether
3,3'-bismaleimidodiphenylsulfone
4,4'-bismaleimidodiphenylsulfone
4,4'-bismaleimidodicyclohexylmethane
3,5-bis(4-maleimidophenyl)pyridine
2,6-bismaleimidopyridine
1,3-bis(maleimidomethyl)cyclohexane
1,3-bis(maleimidomethyl)benzene
1,1-bis(4-maleimidophenyl)cyclohexane
1,3-bis(dichloromaleimido)benzene
4,4'-biscitraconimidodiphenylmethane
2,2-bis(4-maleimidophenyl)propane
1-phenyl-1,1-bis(4-maleimidophenyl)ethane
α,α-bis(4-maleimidophenyl)toluene
3,5-bismaleimido-1,2,4-triazole
and various N,N'-bismaleimides disclosed in U.S. Pat. No. 3,562,223, 4,211,860 and 4,211,861. Bismaleimides can be prepared by methods known in the art, as described in U.S. Pat. No. 3,018,290, for example.

The bisimide resin can contain imide oligomers according to the formula

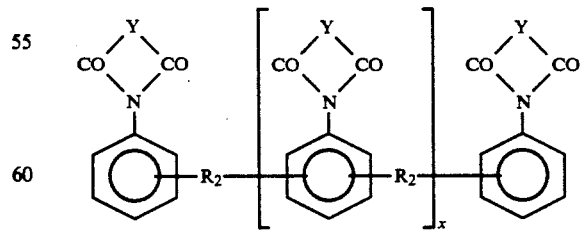

in which x is a number within the range of about 0 to about 3. Such oligomers may be present as an impurity in difunctional bisimides.

The preferred bisimide resin is 4,4'-bismaleimidodiphenylmethane. Suitable N,N'-unsaturated bismaleimide resins are commercially available from Technochemie GmbH as Compimide ® resins, for example.

The invention composition includes a 1,2-dialkylidenecyclobutane, including those which can be described by the structural formula

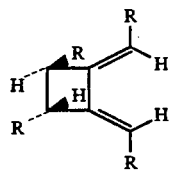

in which each R is selected independently from hydrogen, $C_{1-10}$ alkyl, halo, aryl, alkoxy, aryloxy, alkylthio, arylthio and dialkylamino. The presently preferred 1,2-dialkylidenecyclobutane, because of the superior properties of a bisimide copolymer prepared therewith, is 1,2-dimethylenecyclobutane, which is defined by the above formula when each R is hydrogen.

In general, dialkylidenecyclobutanes can be prepared by the thermal dimerization of the corresponding allenes in a recirculating hot-tube reactor. Specifically, the process will generally be carried out by circulating a stream of gaseous allene through a tube reactor at 450°–600° C. with a residence time in the hot zone of 0.1 to 10 seconds. Downstream from the hot zone, the stream is cooled sufficiently to condense the dialkylidenecyclobutane. Unchanged allene (combined with a fresh makeup stream) is recirculated back to the hot zone by a pump. Such a process is described for 1,2-dimethylenecyclobutane in Chernykh et al., *Neftepererab. Neftekhim.*, 1981 (7), 48–50. Synthesis of 1,2-dimethylenecyclobutane is also illustrated in Example 1 herein. The allene starting material can be produced by pyrolysis of isobutylene or by isolation from a hydrocarbon mixture such as a refinery cracker stream.

The invention composition includes a reactive triene characterized by a conjugated diene moiety capable of unhindered Diels-Alder reaction with the Y moiety of the above-described bisimide and an isolated double bond separated from the conjugated pair by a chemical linking group. Such trienes can be represented by one of the formulas I and II:

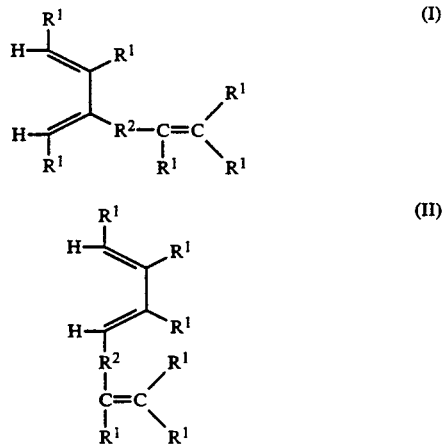

in which each $R^1$ is selected independently from hydrogen and $C_{1-3}$ alkyl, and $R^2$ is a divalent linking group. $R^2$ can be, for example, alkylene, preferably $C_{2-12}$ alkylene; $(CH_2)_nR^3(CH_2)_n$; and $O-R^3-O-$, in which n is an integer from 1 to about 6 and $R^3$ is $C_{1-12}$ alkylene, carbonyl, phenylene, and the like. The preferred $R^2$ linking group is $C_{2-12}$ alkylene, as in myrcene and trans-1,3,7-octatriene. The conjugated diene group must be capable of Diels-Alder reaction with the Y moiety of the bisimide and must not contain substituents in positions which would block the approach of a Diels-Alder dienophile when the diene group is in the cisoid confirmation, as in cis-1,3,7-octatriene, for example. The isolated double bond should be adjoined by at least one hydrogen-bearing carbon atom. Because of the fracture toughness and high-temperature properties achievable in the resulting bisimide copolymer, myrcene is the preferred triene comonomer.

The polyimide, triene and 1,2-dialkylidenecyclobutane monomers may be combined in any manner desired, such as melt, solution or powder blending. The preferred technique, when sufficiently large quantities of monomers are used, involves heating a mixture of the solid polyimide and triene and the liquid 1,2-dialkylidenecyclobutane with stirring at a temperature above the respective melting points but below the polymerization temperature of any monomer, until the mixture becomes a homogeneous melt. The melt may optionally be held at temperatures above about 120° C. for desired periods of time in a process of prepolymerization to increase the crystallization resistance of the melt and/or to increase its viscosity to desired levels. The mixture can then be poured directly into a mold for polymerization, or it can be cooled for later polymerization. For small quantities of monomers, however, excessive amounts of the dialkylidenecyclobutane may volatilize during the melt reaction, upsetting the desired stoichiometric balance. In these cases, it is preferable for the monomer mixture to be processed in a two-step process in which the monomer mixture is reacted in a solvent, with the solvent then evaporated and the adduct melted and cured to solid polymer without solvent.

The relative amounts of the monomers will depend upon the cured and uncured properties desired. In general, optimum properties will be achieved with a ratio of moles (dialkylidenecyclobutane +1.5×triene) : bisimide within the range of about 0.5:1 to about 2:1, preferably about 0.8:1 to about 1.5:1.

The composition may contain an optional free radical inhibitor to inhibit free radical polymerization of the bisimide monomer. Generally, the free radical inhibitor will be present in the composition in an amount within the range of about 0.0002 to about 0.02 moles per mole of the bisimide, preferably from about 0.001 to about 0.01 moles. The free radical inhibitor can be added to the monomers in any manner effective for intimate blending of the monomers and free radical inhibitor. Free radical inhibitors include phenols such as t-butylcatechol, hydroquinone and p-methoxyphenol; quinones such as 1,4-benzoquinone and 1,4-naphthoquinone; polynitro aromatics such as picric acid and 2,4,6-trinitrotoluene; hydroxylamines such as diethylhydroxylamine; stable radicals such as di-t-butylnitroxide or diphenylpicrylhydrazyl; and certain polycyclic heterocycles such as phenothiazine. The preferred free radical inhibitor is phenothiazine.

Polymerization is effected by heating the mixture to a temperature effective to initiate opening of the cyclobutene ring (formed by the initial Diels-Alder reaction of the diene group of the dialkylidenecyclobutane with the dienophilic double bond) to form a transient diene which rapidly reacts with available maleimide groups. This temperature is generally at least about 150° C., preferably about 180° to about 350° C., held for a time of about 0.5 hour or more (with the required cure time dependent on the temperature-staging program used).

In order to achieve optimum properties, a mixture of the monomers and free radical inhibitor is heated at a temperature near or above the ultimate (fully-cured) glass transition temperature of the copolymer for a time sufficient to achieve essentially complete reaction of the monomers. "Essentially complete" reaction of the monomers has been reached when no further reaction exotherm is observed by differential scanning calorimetry (DSC) upon heating the copolymer. The time of the heat treatment, or "post-cure," will vary depending upon the monomers, the degree of pressure applied and any pre-curing of the monomer mixture. Preferably, this post-cure is at or above the ultimate Tg, but will always be at a temperature lower than the temperature at which degradation of the copolymer will occur at significant rates.

The copolymers are useful in adhesives, coatings and as resin matrices for composites in aerospace and electronics applications, including large structural parts and circuit boards. Based on their long shelf life and relatively low melting point, some of the uncured mixtures are useful for making tacky prepregs which can then be molded into composites. They are also suitable for low-solvent or solventless liquid resin processing methods such as filament winding, resin transfer molding and pultrusion if the mixtures are heated to provide sufficiently low viscosity for fiber impregnation.

Electrical applications for the invention compositions include encapsulation of electronic devices and electrical lamination for circuit board manufacture. In encapsulation, the composition will usually be combined, generally by melt-blending, with a suitable inert filler such as particulate silica. For lamination, the composition will be applied, in organic solution or in a solventless melt, to a suitable reinforcement such as glass fiber, and partially cured to form an electrical prepreg, which will subsequently be fabricated into a fully-cured laminate.

For preparation of reinforced laminate materials, a fibrous substrate of glass, carbon, quartz, poly(p-phenyleneterephthalamide), polyester, polytetrafluoroethylene, poly(p-phenylenebenzobisthiazole), boron, paper or like material, in chopped, mat or woven form, is impregnated with a bisimide/dialkylidenecyclobutane composition in molten or solution form. A prepreg is formed by heating the impregnated substrate in an oven at a temperature sufficient to remove the solvent and to partially cure without gelation, or "B-stage," the resin system, generally about 120° C. to about 180° C., preferably about 135° to about 175° C., for a time of up to about 2 hours, preferably about 10 to about 40 minutes. A laminate is fabricated by subjecting a set of layered prepregs to conditions effective to cure the resins and to integrate the prepregs into a laminated structure. The laminate can optionally include one or more layers of a conductive material such as copper.

Laminating generally involves subjecting the prepregs to a temperature above about 175° C., preferably from about 180° to about 350° C., for a time of at least about 10 minutes, at a pressure within the range of about 50 to about 500 psi.

For some laminating applications, it may be advantageous to heat treat, or upstage, the monomer mixture prior to application to a laminating substrate, particularly if the mixture will be stored prior to use. Suitable heat treatment involves subjecting the mixture to an elevated temperature for a time sufficient to cause sufficient reaction and viscosity increase to inhibit crystallization of either or both monomers from the mixture upon storage, but not sufficient to gel the composition. Such heat treatment conditions generally include a temperature of at least about 120° C., preferably about 135° to about 175° C., for a time of at least about 10 minutes, preferably about 12 to about 90 minutes. The resulting mixture will be less tacky and less susceptible to crystallization of the components with storage.

EXAMPLE 1

Preparation of 1,2-Dimethylenecyclobutane.

A recirculating apparatus for the thermal dimerization of allene was designed as follows. The heated reactor was a bank of approximately 110 segments (each about 30 cm long) of stainless steel tubing 1.27 cm in outside diameter. The segments were arranged vertically in series and connected to one another by U-shaped stainless steel connectors to which they were welded. The volume of the heated portion of the reactor was about 3.4 liters. The bank of tubes was immersed in a fluidized bed of aluminum oxide particles. Thermocouples wedged between the connectors of the reactor at various points allowed one to monitor the wall temperature of different segments of the reactor.

Downstream from the reactor was a cold trap containing a cooling fluid at approximately −65° C. above a flask which functioned as a gas-liquid separator. Downstream from the first trap was a second trap filled with dry ice in dichloromethane, guarding the outlet to the system (through an oil bubbler) to condense any allene which otherwise could have escaped from the system. Condensed allene from this second trap fell into the gas-liquid separator. The condensed material (allene dimers and some of the allene) from the traps fell to the bottom of the separator and then flowed through a fluoropolymer tube into a reservoir for liquid allene and allene dimers. Sufficient heat was applied to this reservoir to keep the allene boiling gently. The allene not condensed by the cold traps was combined with that evaporating from the reservoir. This stream of recovered allene was passed through a filter into a diaphragm pump which recirculated the allene back into the hot tube. A makeup stream of fresh allene from a cylinder was also introduced into the loop just upstream from the recirculation pump.

The system was first purged with nitrogen. The power to the fluidized bed was turned on and its temperature was brought to 450°–470° C. Allene was introduced into the system from the allene cylinder at a rate of 80–100 g/hr. The allene supply from the cylinder was shut off two to three hours before the end of a dimerization run in order that the allene present in the system could be used up, with little allene remaining in the reservoir at the end. At the end of the day, the power to the fluidized bed was turned off, the system was allowed to cool, and the accumulated dimer was poured into a bottle and weighed. Approximately 3 g of phenothiazine was added per kilogram of dimer to inhibit polymerization of the 1,2-dimethylenecyclobutane. The crude dimer was then analyzed by gas chromatography for peaks corresponding to two allene dimers, 1,2-dimethylenecyclobutane (1,2-DMCB) and 1,3-dimethylenecyclobutane (1,3-DMCB), and a component shown by mass spectrometry to have a molecular formula of $C_9H_{12}$ (an allene trimer). Data from seven hot tube reaction runs are shown in Table 1.

TABLE 1

| Reaction # | Reaction time, hr. | Allene used, g | Crude dimer produced, g | Crude yield, % | GC analysis 1,3-DMCB, % | 1,2-DMCB, % | $C_9H_{12}$ peak, % |
|---|---|---|---|---|---|---|---|
| 1 | 8.0 | 558 | 443 | 79.4 | 8.4 | 67.0 | 15.0 |
| 2 | 15.8 | 1197 | 881 | 73.6 | 8.1 | 75.0 | 11.0 |
| 3 | 11.3 | 862 | 753 | 87.3 | 8.3 | 73.4 | 11.4 |
| 4 | 11.2 | 824 | 647 | 78.5 | 8.3 | 71.6 | 14.0 |
| 5 | 11.8 | 932 | 806 | 86.5 | 8.5 | 68.7 | 15.4 |
| 6 | 11.4 | 909 | 746 | 82.1 | 8.4 | 68.0 | 16.2 |
| 7 | 11.0 | 872 | 724 | 83.0 | 8.5 | 69.0 | 15.7 |

The products of the seven runs in Table 1 were flash-distilled under vacuum to remove tars and were subsequently distilled under reduced pressure in 2.54 cm Oldershaw columns with 30 plates. The resulting distilled fractions and similarly-obtained DMCB cuts were used in the following examples.

EXAMPLE 2

Bis(4-maleimidophenyl)methane (COMPIMIDE ® MDAB) (2508.6 grams) and phenothiazine (7.54 grams) were mixed and wetted thoroughly with myrcene (SCM Glidco P&F grade) (619.8 grams). The wet powder was added in portions to a 3.5-liter stainless steel beaker with a handle held on a hot plate. The mixture was stirred as additional wetted powder was added until the contents were liquid and homogeneous (this required about 10 minutes; maximum liquid temperature reached was 146° C.). The mixture was then poured out into aluminum trays and allowed to cool to room temperature and solidify. The solidified adduct was broken into chunks and used in the following section.

Four mixtures (mixtures 1-4 in Table 2 below) were prepared as follows. To 500-mL glass bottles were added the amounts shown of COMPIMIDE ® MDAB (the bismaleimide of 4,4'-methylenedianiline), a distilled dimethylenecyclobutane fraction containing mostly 1,2-isomer, the COMPIMIDE ® MDAB-myrcene adduct prepared above, phenothiazine and Monsanto PC-1344 defoamer (an acrylic oligomer, added to prevent excessive foaming during vacuum degassing and to enable the preparation of void-free castings) along with 180 grams of dichloromethane solvent. In these mixtures, the number of moles of bismaleimide (other than that pre-incorporated into the myrcene adduct) was equal to the number of moles of 1,2-dimethylenecyclobutane. The bottles were placed on rollers and rolled overnight (or longer) at room temperature to allow completion of the first-stage Diels-Alder reaction between the 1,2-dimethylenecyclobutane and the maleimide groups of the bismaleimide. The mixtures were poured into 250-mL Erlenmeyer flasks with a vacuum connection. The flasks were placed in a 125°-150° C. oil bath and the contents were swirled as solvent, 1,3-dimethylenecyclobutane, and other volatile unreacted materials were removed, first at atmospheric pressure and then under mechanical pump vacuum for a few minutes until bubbling had essentially stopped. The degassed molten mixtures were then poured into a two-piece rectangular stainless steel mold with a ⅛" (3.175 mm) thick cavity, with the mold parts separated by a gastight silicone rubber gasket such that the mold could be pressurized during cure. A few grams of each uncured sample were kept as a retain for characterization of uncured properties. The mold was then placed into an oven and pressurized with nitrogen to 750 kPa (~95 psig) and the systems were cured for one hour at 150° C., followed by ramping linearly to 290° C. over a period of 3.5 hours and then holding for one hour at 290° C. A fifth casting (#5) was prepared by curing the bismaleimide-myrcene adduct prepared above without adding any DMCB or additional bismaleimide. Properties of the castings (and the uncured systems) are shown in Table 2.

One can see from Table 2 that incorporation of the myrcene into the BMI-DMCB composition lowers the temperature at which a desirable fiber impregnation viscosity of 1 Pas is reached. This temperature, sometimes defined as the lower limit of the "processing window," is lowered in line with the percentage of myrcene incorporated into the system. The temperature at which a viscosity of 1 Pas is reached again with rising temperature, sometimes defined as the upper limit of the "processing window," is similarly raised with increasing myrcene incorporation, widening the processing window further. Tg is also raised somewhat, and MEK and dichloromethane absorption are lowered somewhat, with increasing replacement of DMCB by myrcene. Low room temperature dry modulus is a disadvantage of some unmodified DMCB-BMI systems. One can see from Table 2 that myrcene incorporation similarly raises room temperature dry modulus in line with the extent of replacement of DMCB by myrcene (93° C. wet modulus is also raised slightly). Even though myrcene addition produced loss of toughness, all the BMI/DMCB/myrcene blends had fracture toughness values higher, and two considerably higher, than that of the control BMI/myrcene copolymer containing no DMCB (casting #5).

TABLE 2

| Experiment # | 1 | 2 | 3 | 4 | 5 |
|---|---|---|---|---|---|
| Composition: | | | | | |
| Bismaleimide, grams | 73.10 | 61.29 | 40.86 | 20.43 | |
| moles | 0.2040 | 0.1710 | 0.1140 | 0.0570 | |
| 1,2-Dimethylenecyclobutane (DMCB): | | | | | |
| Crude distillate, grams | 19.78 | 15.62 | 10.41 | 5.21 | |
| % 1,2-isomer in crude distillate (GC area) | 82.606 | 87.723 | 87.723 | 87.723 | |
| Net 1,2-isomer, grams | 16.34 | 13.70 | 9.13 | 4.57 | |

TABLE 2-continued

| Experiment # | 1 | 2 | 3 | 4 | 5 |
|---|---|---|---|---|---|
| moles | 0.2039 | 0.1710 | 0.1140 | 0.0570 | |
| Bismaleimide/myrcene adduct, g | | 25 | 50 | 75 | 100 |
| Phenothiazine, g | 0.20 | 0.20 | 0.20 | 0.20 | 0.20 |
| Monsanto PC-1344 defoamer, g | 0.20 | 0.20 | 0.20 | 0.20 | 0.20 |
| *Uncured properties:* | | | | | |
| Temperature, °C., at which viscosity reaches 1 Pa.s on heatup | 125 | 124 | 120 | 109 | 101 |
| Temperature, °C., at which viscosity again exceeds 1 Pa.s | 193 | 206 | 219 | 266 | 282 |
| *Cured properties:* | | | | | |
| Rheometrics tan δ peak, °C. | 291 | 295 | 325 | 345 | 345 |
| *R.T. dry flexural (ASTM D-790):* | | | | | |
| Yield strength, MPa | 122 ± 1 | 123 ± 1 | 125 ± 2 | 126 ± 9 | 124 ± 6 |
| Tangent modulus, GPa | 2.67 ± 0.02 | 2.73 ± 0.03 | 2.85 ± 0.05 | 2.98 ± 0.04 | 3.06 ± 0.08 |
| Break elongation, % | >6.5 | >6.5 | >6.5 | >6.0 | 5.2 ± 0.4 |
| *93° C. wet flexural (ASTM D-790):* | | | | | |
| Yield strength, MPa | 81 ± 1 | 82 ± 2 | 86 ± 11 | 93 ± 1 | 85 ± 13 |
| Tangent modulus, GPa | 2.33 ± 0.02 | 2.31 ± 0.02 | 2.38 ± 0.07 | 2.34 ± 0.02 | 2.41 ± 0.05 |
| Break elongation, % | >6.5 | >6.5 | >5.0 | >6.0 | 4.1 ± 1.0 |
| Compact tension fracture toughness, $K_q$, MPa-m$^{\frac{1}{2}}$ (ASTM E 399-83) | 2.93 ± 0.13 | 1.61 ± 0.09 | 1.04 ± 0.03 | 0.75 ± 0.04 | 0.68 ± 0.01 |
| Dielectric constant, 1 MHz (ASTM D229/15) | 3.40 | 3.22 | 3.12 | 3.33 | 3.33 |
| Dissipation factor, 1 MHz (ASTM D229/15) | 0.0156 | 0.0139 | 0.0125 | 0.0139 | 0.0138 |
| *93° C. $H_2O$ pickup, %:* | | | | | |
| 1 day | 1.66 | 2.38 | 2.76 | 2.25 | 2.21 |
| 2 weeks | 2.28 | 3.00 | 3.35 | 2.71 | 2.55 |
| *Room temp. methyl ethyl ketone pickup, %:* | | | | | |
| 1 day | 0 | 0 | 0 | 0 | 0 |
| 2 weeks | 1.69 | 0.55 | 0 | 0 | 0 |
| *Room temp. $CH_2Cl_2$ pickup, %:* | | | | | |
| 1 day | 169 | disint. | 17.1 | 6.11 | 3.24 |
| 2 weeks | 179 | | 75.2 | 61.4 | 54.5 |

<sup>a</sup>Only the 1,2-isomer contained in the crude 1,2-dimethylenecyclobutane distillate was considered as part of total system solids. Other components in the distillate were made up primarily of Diels-Alder unreactive, 1,3-isomer and were not counted as contributing to solids.

I claim:

1. A composition comprising
   (a) a difunctional bisimide of an unsaturated dicarboxylic acid represented by the formula

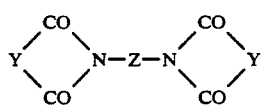

in which Y is a substituted or unsubstituted divalent moiety containing at least 2 carbon atoms and a carbon-carbon double bond, and Z is a divalent linking group;
   (b) a triene which contains both a conjugated diene moiety capable of unhindered Diels-Alder reaction with a Y group of the bisimide and a carbon-carbon double bond separated from the conjugated pair by a divalent linking group; and
   (c) a 1,2-dialkylidenecyclobutane represented by the formula

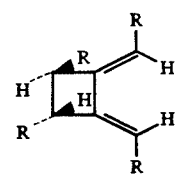

in which each R is selected independently from the group consisting of hydrogen, $C_{1-10}$ alkyl, halo, aryl, alkoxy, aryloxy, alkylthio, arylthio and dialkylamino.

2. The composition of claim 1 in which the triene is represented by one of the formulas I or II:

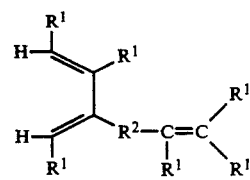

(I)

-continued

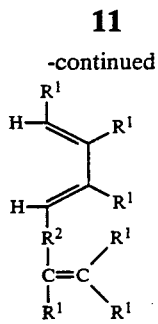 (II)

in which each $R^1$ is selected independently from the group consisting of hydrogen and $C_{1-3}$ alkyl and $R^2$ is a divalent linking group.

3. The composition of claim 2 in which component (a) is a bismaleimide.

4. The composition of claim 3 in which component (c) is 1,2-dimethylenecyclobutane.

5. The composition of claim 4 in which the molar ratio [dimethylenecyclobutane+(1.5×triene)]:bismaleimide is within the range of about 0.5:1 to about 2:1.

6. The composition of claim 1 in which component (a) comprises 4,4'-bismaleimidodiphenylmethane and component (c) is 1,2-dimethylenecyclobutane.

7. The composition of claim 3 which further comprises an effective amount of a free radical inhibitor for the bismaleimide.

8. The composition of claim 1 which further comprises a fibrous reinforcing agent.

9. The composition of claim 1 which further comprises particulate silica.

10. A polymeric composition comprising the product of contacting, at a temperature of at least about 180° C., monomers comprising (a) a bisimide of an unsaturated dicarboxylic acid represented by the formula

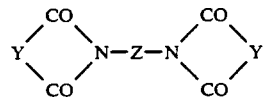

in which Y is a substituted or unsubstituted divalent moiety containing at least 2 carbon atoms and a carbon-carbon double bond, and Z is a divalent linking group;

(b) a triene which contains both a conjugated diene moiety capable of unhindered Diels-Alder reaction with a Y group of the bisimide and a carbon-carbon double bond separated from the conjugated pair by a divalent linking group; and (c) a 1,2-dialkylidenecyclobutane represented by the formula

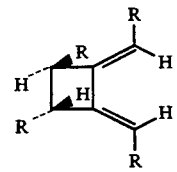

in which each R is selected independently from the group consisting of hydrogen, $C_{1-10}$ alkyl, halo, aryl, alkoxy, aryloxy, alkylthio, arylthio and dialkylamino.

11. The composition of claim 10 in which the molar ratio [dialkylidenecyclobutane+(1.5×triene)]:bisimide is within the range of about 0.8:1 to about 1.2:1.

12. The composition of claim 10 in which the triene is myrcene.

13. The composition of claim 10 in which component (a) is a bismaleimide and component (c) is 1,2-dimethylenecyclobutane.

14. The composition of claim 13 in which the triene is myrcene.

15. A prepreg comprising the composition of claim 1 and a fibrous substrate.

16. A process for preparing a copolymer comprising the steps of (a) preparing a mixture of a difunctional bisimide of an unsaturated dicarboxylic acid, myrcene and from about 0.6 to about 2.5 moles, per mole of the difunctional bisimide, of a 1,2-dialkylidenecyclobutane represented by the formula

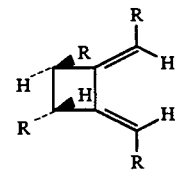

in which each R is selected independently from the group consisting of hydrogen, $C_{1-10}$ alkyl, halo, aryl, alkoxy, aryloxy, alkylthio, arylthio and dialkylamino; and (b) heating said mixture to a temperature within the range of about 180° to about 350° C. for at least about 0.5 hour.

17. The process of claim 16 in which the difunctional bisimide comprises 4,4'-bismaleimidodiphenylmethane.

18. The process of claim 17 in which the difunctional bisimide further comprises at least one of 2,4-bismaleimidotoluene or 1,3-bismaleimidobenzene.

19. The process of claim 16 in which said mixture further comprises phenothiazine.

* * * * *